(12) United States Patent  
Elencwajg

(10) Patent No.: US 8,996,135 B2  
(45) Date of Patent: *Mar. 31, 2015

(54) DEVICE AND METHOD FOR INSERTING A CARDIAC CATHETER

(76) Inventor: Benjamin Daniel Elencwajg, Buenos Aires (AR)

(*) Notice: Subject to any disclaimer, the term of this patent is extended or adjusted under 35 U.S.C. 154(b) by 175 days.

This patent is subject to a terminal disclaimer.

(21) Appl. No.: 13/091,781

(22) Filed: Apr. 21, 2011

(65) Prior Publication Data

US 2011/0257629 A1    Oct. 20, 2011

Related U.S. Application Data

(63) Continuation-in-part of application No. 12/289,168, filed on Oct. 22, 2008, now Pat. No. 8,000,809.

(30) Foreign Application Priority Data

Oct. 23, 2007  (AR) .......................... P200701040682

(51) Int. Cl.
*A61N 1/372* (2006.01)
*A61N 1/05* (2006.01)

(52) U.S. Cl.
CPC ........................ *A61N 1/056* (2013.01)
USPC ............................ 607/122; 607/119; 600/374

(58) Field of Classification Search
CPC ....................... A61N 1/056; A61N 2001/058
USPC ................................ 607/9, 119, 122; 600/374
See application file for complete search history.

(56) References Cited

U.S. PATENT DOCUMENTS

| 1,207,479 | A | * | 12/1916 | Bisgaard | 604/104 |
|---|---|---|---|---|---|
| 4,299,228 | A | * | 11/1981 | Peters | 604/122 |
| 4,411,276 | A | * | 10/1983 | Dickhudt et al. | 607/116 |
| 4,538,624 | A | * | 9/1985 | Tarjan | 600/517 |
| 5,171,233 | A | * | 12/1992 | Amplatz et al. | 604/540 |
| 5,814,029 | A | * | 9/1998 | Hassett | 604/528 |
| 5,836,947 | A | * | 11/1998 | Fleischman et al. | 606/47 |
| 6,016,811 | A | * | 1/2000 | Knopp et al. | 128/898 |
| 6,217,528 | B1 | * | 4/2001 | Koblish et al. | 600/585 |
| 6,254,610 | B1 |   | 7/2001 | Darvish et al. |   |
| 6,430,426 | B2 |   | 8/2002 | Avitall |   |
| 6,517,550 | B1 | * | 2/2003 | Konya et al. | 606/113 |
| 6,613,046 | B1 | * | 9/2003 | Jenkins et al. | 606/41 |
| 7,130,699 | B2 | * | 10/2006 | Huff et al. | 607/116 |
| 7,218,970 | B2 | * | 5/2007 | Ley et al. | 607/116 |
| 7,529,589 | B2 |   | 5/2009 | Williams et al. |   |

(Continued)

*Primary Examiner* — Carl H Layno
*Assistant Examiner* — Eugene Wu
(74) *Attorney, Agent, or Firm* — Carl M. Napolitano; GrayRobinson, P.A.

(57) ABSTRACT

A device and method for implanting a catheter between the left atrium and/or left ventricle of the heart from a prepectoral region through a less invasive and lower-risk approach is provided that allows the implantation of the catheter in the left cardiac chambers through a femoral approach atrial transseptal puncture, and the removal of the catheter proximal end by a retrograde venous route. The device includes a transseptal sheath for slidably carrying the catheter, an elongate pulling element attached to a proximal end of the catheter, a runner slidable within the transseptal sheath and operable for biasing against the proximal end of the cardiac catheter, and a loop catheter having a loop formed at one end thereof, wherein the loop is dimensioned for receiving the transseptal sheath and for receiving the elongate pulling element therein when the loop and the elongate pulling element are separated from the transseptal sheath.

9 Claims, 15 Drawing Sheets

(56) References Cited

U.S. PATENT DOCUMENTS

| | | | |
|---|---|---|---|
| 7,539,542 B1* | 5/2009 | Malinowski | 607/37 |
| 7,753,696 B2* | 7/2010 | Hoecke et al. | 439/92 |
| 8,065,020 B2* | 11/2011 | Ley et al. | 607/116 |
| 2004/0186542 A1* | 9/2004 | van Venrooij et al. | 607/116 |
| 2004/0260370 A1* | 12/2004 | Ley et al. | 607/115 |
| 2005/0004605 A1* | 1/2005 | Zheng et al. | 607/5 |
| 2006/0030918 A1* | 2/2006 | Chinn et al. | 607/117 |
| 2006/0224225 A1* | 10/2006 | Ransbury et al. | 607/122 |
| 2007/0191920 A1* | 8/2007 | Ley et al. | 607/116 |
| 2011/0022057 A1* | 1/2011 | Eigler et al. | 606/129 |

\* cited by examiner

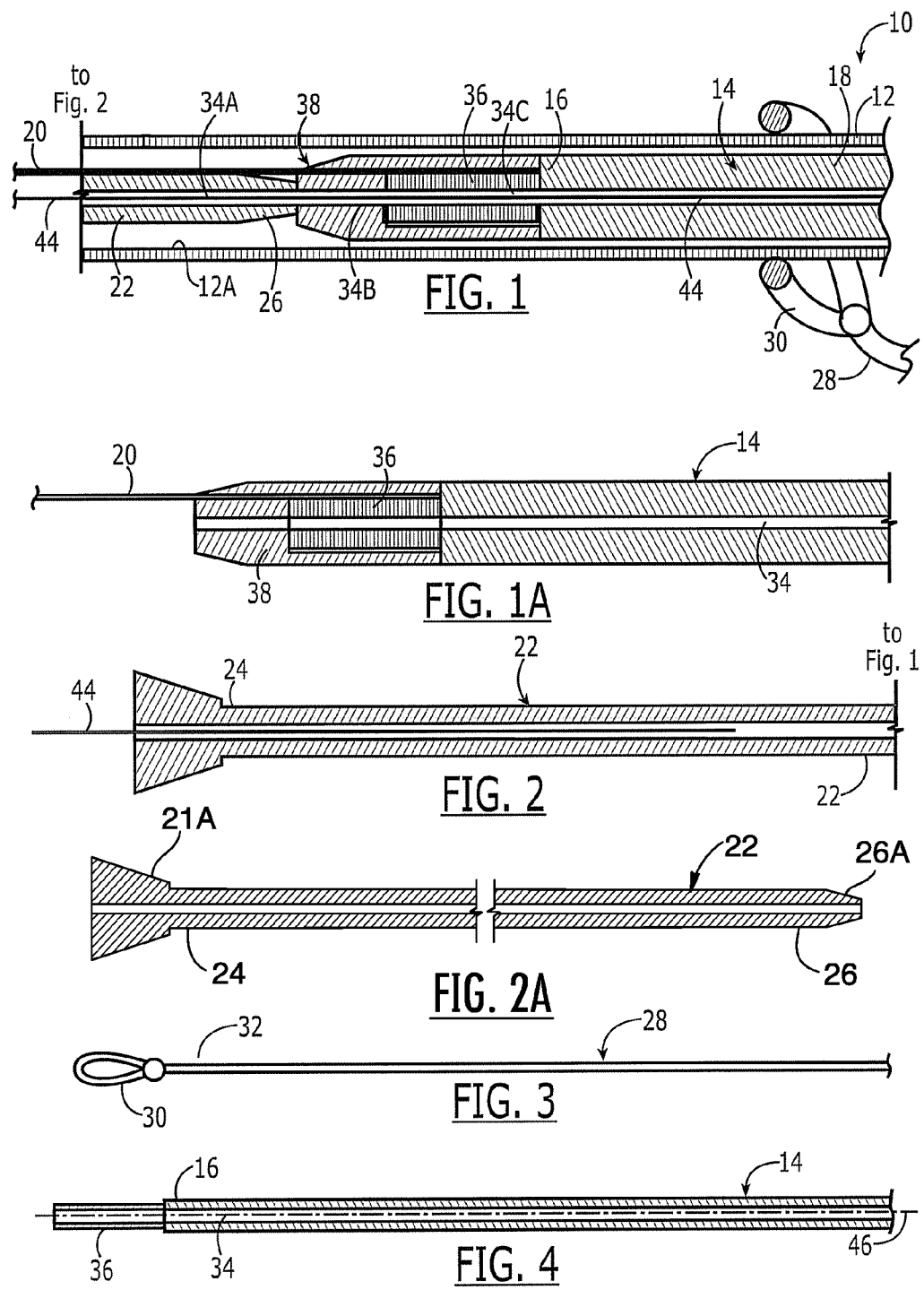

DEVICE AND METHOD FOR INSERTING A CARDIAC CATHETER

CROSS-REFERENCE TO RELATED APPLICATIONS

This application claims priority to U.S. application Ser. No. 12/289,168 for a Method of Inserting a Cardiac Catheter having filing date of Oct. 22, 2008, now U.S. Pat. No. 8,000,809, which itself claims priority to Application Serial No. P 2007 01040682 filed in Argentina on Oct. 23, 2007, the disclosures of which are incorporated by reference in their entirety and commonly owned.

FIELD OF INVENTION

The invention generally relates to cardiac surgery and cardiac implantations and more particularly to a device and method for the intracavitary implant of a catheter in the left atrium and/or ventricle through a femoral approach for an atrial transseptal puncture, and removal of the catheter proximal end by a retrograde venous route toward the prepectoral region.

BACKGROUND

Methods to insert catheters in left atrium and/or ventricles through surgery such as an outer cut on the chest wall are well known and known to be a very sensitive and high-risk approach from a patient's point of view, and requires close post surgical control, or in the venous system of the heart, which method is often impossible to carry out and requires considerable expertise in performance, thus limiting general application. Currently, there exists a technique, which includes intracavity stimulation of the left ventricle. However, it is complex and difficult to perform.

The insertion of catheters in right atrium and/or ventricles is currently performed in a simple way by inserting the catheter in the subclavian, cephalic or jugular vein after a simple puncture and by means of a catheter introducer. However, this is not the case when the catheter is to be inserted in the left atrium and ventricle, because there is no direct path through the mentioned veins. Typically, surgery is required in order to insert the catheter outside (the epicardial region) the atrium and/or the left ventricle, including a cut in the external chest wall. Such a procedure entails a great risk. On the other hand, this technique offers a very restricted access to the left atrium and ventricle, thus preventing the choice of a preferred implantation site.

There is an option of inserting the catheter in the venous system of the heart, which is often impossible to perform due to the morphologic structure of the system. Such option requires considerable expertise in technique and is limiting in its general application.

Another technique uses the transseptal puncture of the atrium to insert the catheter by the antegrade venous route. This technique requires multiple passing of sheaths, balloon catheters and lines through the interatrial septum, successive dilations of the interatrial septum, and typically more, which turn it complex and increases risk to the patient.

SUMMARY

The present invention is directed to solving the problems as addressed above and in one embodiment provides a device for placing the catheter through intracavitary implantation into the left atrium and/or ventricle using the venous system, without external surgical openings, and only by making a single femoral approach puncture on the septum between the right and left atria, and removal of the catheter proximal end, an end that may be connected to a pacemaker or any other device that might be implanted, in the prepectoral region by the retrograde venous route.

One embodiment of the invention may comprise a cardiac catheter slidably carried within a transseptal sheath, an elongate pulling element attached to a proximal end of the cardiac catheter, a runner slidable within the transseptal sheath and operable for biasing against the proximal end of the cardiac catheter, wherein movement is provided thereto, and a loop catheter having a loop formed at one end thereof, wherein the loop is dimensioned for loosely receiving the transseptal sheath therein and for receiving the elongate pulling element therein when the loop and the elongate pulling element are separated from the transseptal sheath.

A method aspect of the invention may comprise implanting a catheter into the heart by extending the catheter into an inferior vena cava, pushing the proximal end of the catheter for placing the distal end thereof into a right atrium of the heart, continuing to push the proximal end of the catheter for passing the distal end through a puncture in the interatrial septum of the heart, positioning the distal end of the catheter in the left atrium or ventricle, as desired, and pulling the proximal end of the catheter into the superior vena cava. The proximal end of the catheter may be extracted from the body through the subclavian vein or tributaries of the superior vena cava, as desired.

A desirable feature of the invention is its simplicity and safety, since the elements are inserted by simple venous and femoral approach transseptal punctures. By way of example methods according to the teachings of the present invention do not require a chest opening for implantation. Devices used do not require use of the venous system of the heart. The catheter may be inserted into the left atrium and/or ventricle by a single femoral approach transseptal puncture on the interatrial septum of the heart. There is no need for additional dilations of the interatrial septum puncture. Embodiments of the invention do not require successive passing of elements through the interatrial septum and allows the choice from among several sites of the best site on each patient to implant the catheter in the left atrium and ventricle. Further, the surgical techniques required are commonly used and broadly known.

One embodiment of the invention provides for the implantation of an intracavity catheter in the left atrium and/or ventricle through a single femoral approach transseptal puncture on the atrium, and the removal of the proximal end of the catheter by the retrograde venous route toward the prepectoral region and optionally outside the body.

BRIEF DESCRIPTION OF DRAWINGS

The advantages of the invention, which should not be limited to the brief description above, will become more apparent and the invention itself better understood by reference to the following embodiments of the invention herein described by way of example of possible embodiments with reference to the accompanying drawings in which:

FIG. 1 is a partial longitudinal cross-sectional view illustrating a device of one embodiment of the invention;

FIG. 1A is a cross-sectional view of selected elements illustrated in FIG. 1, including a connector carried at a proximal end of a cardiac catheter, the connector inserted into a fastener, and a pulling element affixed between them, by way of example;

FIG. 2 is a longitudinal crossectional view of a mandrel partially inserted into a runner;

FIG. 2A is a longitudinal cross-sectional view of the runner according to the teachings of the present invention;

FIG. 3 is a plan view of a loop catheter according to the teachings of the invention, the loop catheter dimensioned to be inserted in a subclavian vein;

FIG. 4 is a cross-sectional view of a tubular cardiac catheter according to the teachings of the present invention, which cardiac catheter is dimensioned to be inserted by a femoral route, which proximal end is removable by a subclavian, jugular or cephalic veins or the like;

FIG. 22, illustrates the loop catheter retrograde pull of the pulling element joined to the fastener and the proximal end of the cardiac catheter inside the superior vena cava, the direction being identified with arrow, the transseptal sheath remaining inside the inferior vena cava, wherein the transseptal sheath is later removed retrogradely;

FIG. 23, illustrates the retrograde pull of the fastener and the proximal end of the cardiac catheter by the pulling element into the superior vena cava;

FIG. 26, illustrates one desired position of the proximal end of the cardiac catheter outside the human body, wherein the distal end of the cardiac catheter is desirably located inside the left atrial chamber, or passing through the mitral valve at different preselected localizations in the left ventricle, as identified with dotted lines, and ready to connect a pacemaker, by way of example.

DESCRIPTION OF EMBODIMENTS

Figure 5:
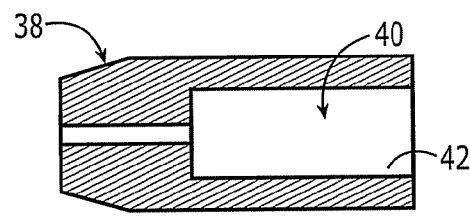
FIG. 5 is a longitudinal cross-sectional view of the fastener illustrated in FIG. 1, which fastener is dimensioned to be inserted by a femoral route.

Embodiments of the invention are herein described by way of example for devices and methods for implanting an endocavitary catheter into the left atrium and/or into the left ventricle via a femoral atrial transseptal puncture approach and the exteriorization of its proximal end to a prepectoral region. The catheter may be permanently located in the heart as desired.

By way of example and with reference initially to FIGS. 1 and 1A, one embodiment of the invention is herein described as a cardiac implantation device 10 comprising a transseptal sheath 12 and a cardiac catheter 14 slidably carried within the transseptal sheath. The cardiac catheter 14 is herein described as having a proximal end 16 and an opposing distal end 18. An elongate and flexible pulling element 20 is attached to the proximal end 16 of the cardiac catheter 14. With continued reference to FIG. 1 and now to FIGS. 2 and 2A, an elongate runner 22 having a proximal end 24 and an opposing distal end 26 is slidable within the transseptal sheath 12 and is manually operable for biasing against the proximal end 16 of the cardiac catheter 14 for moving the cardiac catheter further into the transseptal sheath 12, as will be further detailed later in this section. By way of example for the runner 22 herein described, a handle 24A is formed on the proximal end 24 of the runner for manual manipulating thereof, and the opposing distal end 26 includes a tapered portion 26A. As will come to the mind of those skilled in the art, the pulling element may comprise surgical suturing, a wire, and another catheter or other suitable element.

With continued reference to FIG. 1 and to FIG. 3, a loop catheter 28 includes a loop 30 formed at a first end 32 thereof. The loop 30 is dimensioned for loosely receiving the transseptal sheath 12 therein and for receiving the elongate pulling element 20 therein when the loop and the elongate pulling element are separated from the transseptal sheath, as will be further detailed later in this section.

As will also be understood by those of ordinary skill in the medical arts, a catheter is a tube that can be inserted into a body cavity, duct, or vessel. Cardiac catheters may allow for stimulation, administration of fluids, drugs or any other type of substance, measure physiological parameters such as temperature, pH, pressure, and the like, and clearly may have multiple functions. Typically, a catheter is a thin, flexible, sometimes tubular, sometimes carrying electrical conductors and/or electrodes. The catheter may be a solid catheter. The cardiac catheter 14 illustrated with reference again to FIG. 1 and to FIG. 4 comprises a tubular catheter having a lumen or passage 34 extending fully therethrough.

With continued reference to FIGS. 1 and 4, and now to FIG. 5, a connector 36 is attached to the proximal end 16 of the cardiac catheter 14 and a fastener 38 is attached to the connector 36. For the embodiment herein described by way of example, the connector 36 is integrally attached to the proximal end 16 of the cardiac catheter 14. Yet further, the fastener 38 comprises an aperture 40 extending therethrough, wherein the connector 36 is secured within a broadened portion 42 of the aperture.

Figure 6:
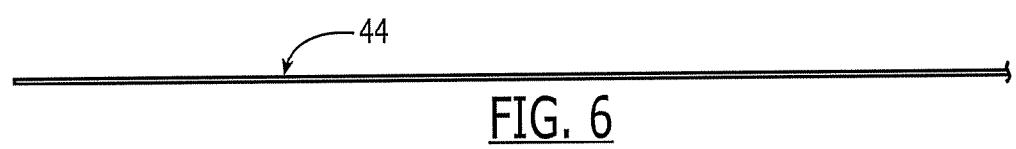
FIG. 6 is a plan view of a mandrel according to the teachings of the present invention.

With continued reference to FIG. 1 and to FIG. 6, the device 10 further comprises an elongate mandrel 44, which may be formed by a surgical wire by way of example, wherein the mandrel may be slidably extended into the passage 34 extending through the cardiac catheter 14 and passages 34A, 34B, 34C, extending through the runner 22, the fastener 38 and the connector 36, respectively. For the embodiment of the device 10, herein described by way of example and as will be further detailed later in this section, the mandrel 44 is used with the tubular cardiac catheter 14 to align the runner 22 with the cardiac catheter 14. As will be appreciated by those of skill in the art, the mandrel 44 forms an integral connection of the runner 22, the fastener 38, the pulling element 20 and the cardiac catheter 14, and keeps the cardiac catheter generally rigid along a central axis 46 thereof to allow the cardiac catheter to move within the transseptal sheath 12 while avoiding kinking and involuntary movement thereof.

The transseptal sheath 12 is sufficiently rigid for providing torque control through movement thereof and sufficiently flexibility for movement through human body apertures, the sheath further having an inner wall 12A sufficient for smoothly receiving the catheter 14, the fastener 38, the pulling element 20 and the runner 22. With such structure to the transseptal sheath 12, those of skill in the art will appreciate use of alternate catheters of various flexibility and rigidity for maneuvering without use of the mandrel 44 as herein described for one preferred embodiment of the invention.

Figure 7:
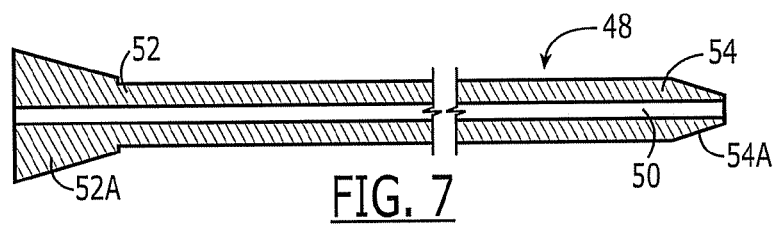
FIG. 7 is a longitudinal cross-sectional view of an aligning device according to the teachings of the present invention, which aligning device is dimensioned to be inserted in a subclavian vein.

While its use may be optional and as will be detailed later in this section, the device 10 may be used in cooperation with an aligning device 48, as illustrated with reference to FIG. 7, having an aperture 50 extending fully therethrough. The aligning device 48 is herein described as including a proximal end 52 and an opposing distal end 54, wherein the distal end 54 may have a tapered portion 54A and is dimensioned for engaging the proximal end 16 of the cardiac catheter 14, and the fastener 38, through a pulling action by the pulling element 20 when extending through the aperture 50, as will be further detailed later in this section. The proximal end 52 of the aligning device 48 may comprise a handle 52A for convenience in manually maneuvering the aligning device 48.

It will be understood by those of ordinary skill in the art that elements may be modified or eliminated and others added without departing from the teachings and spirit of the present invention A method aspect of the invention is herein presented by way of example employing the device 10 above described for implanting the cardiac catheter 14, which catheter is tubular for use in accessing the heart through the cardiac catheter. The cardiac catheter may be permanently placed in the heart. By way of example, an electrical connection from a pacemaker to a location or locations in the left atrium or left ventricle, as will be further detailed below. Alternatively and in keeping with the teachings of the present invention, a solid catheter may be implanted, the solid catheter itself providing an electrical path, or other functions as desired, between the pacemaker and a preselected location in the left atrium and/or left ventricle.

Figure 8:
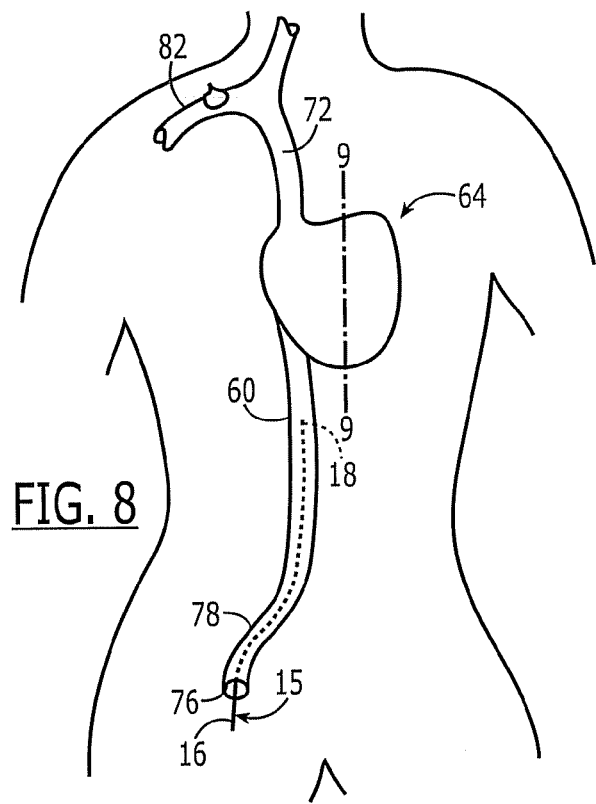
FIG. 8 is a partial diagrammatical view of a human body with a localization of a subclavian vein and a femoral vein, and their relation to the superior vena cava, the inferior vena cava, and the right atrium of the heart.
Figure 9:
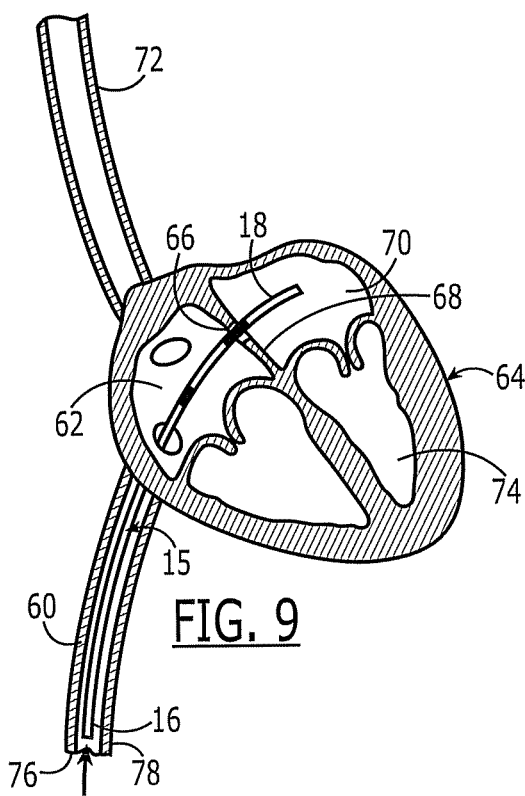
FIG. 9 is a 9-9 cross-sectional view of FIG. 8 partially illustrating details of cardiac chambers, and the superior vena cava and the inferior vena cava entry into the right atrium.
Figure 10:
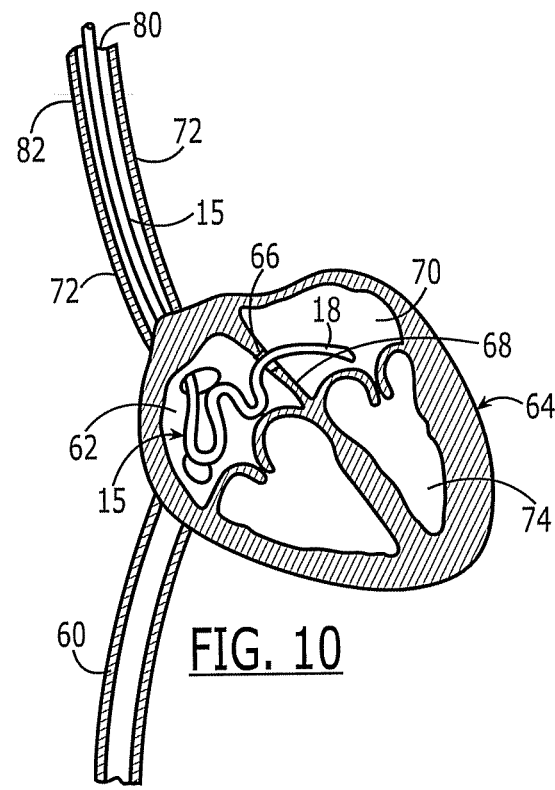
FIG. 10 illustrates a retrograde pull of the proximal end of a catheter into the superior vena cava.

One method for implanting a catheter 15 is herein described, by way of example with reference to FIGS. 8 and 9, as comprising the steps of extending the catheter 15 into an inferior vena cava 60 and pushing the proximal end 16 of the catheter 15 until the distal end 18 of the catheter is positioned within a right atrium 62 of a heart 64. The catheter proximal end 16 is continued to be pushed for passing the distal end 18 of the catheter through a puncture 66 in the interatrial septum 68 of the heart 64 and into a left atrium 70. The proximal end 16 of the catheter 15 is then pulled into a superior vena cava 72, as illustrated with reference to FIG. 10. The distal end 18 of the catheter 15 may also be placed in a left ventricle 74, as desired.

With reference again to FIGS. 8 and 10, as will be further described later in this section, extending the catheter 15 into the inferior vena cava 60 preferably comprises pushing the catheter through a puncture 76 in the femoral vein 78. Pulling the proximal end 16 of the catheter 15 into the superior vena cava 72 preferably comprises accessing the proximal end of the catheter through a puncture 80 in a subclavian vein 82. Further, the puncture 66 in the interatrial septum 68 may be made by puncturing the interatrial septum by a femoral atrial transseptal puncturing procedure. Further, the proximal end 16 of the catheter 15 may be positioned outside the vein 82, and optionally within a prepectoral region of a body 86 for operation with an implantable device 88, such as a pacemaker or the like, proximate the proximal end 16 of the catheter 15, as illustrated with reference to FIG. 11.

While the subclavian vein 82 is herein used to explain an embodiment of the invention, it will be understood by those of skill in the art any suitable vein tributary of the superior vena cava may be used. Such tributaries may include the subclavian vein 82, as herein described by way of example, an axilar, cephalic or jugular vein as desired. Further, such veins may be left or right veins.

One method, as herein described by way of example, is directed to implanting the tubular cardiac catheter 14 using the device 10, earlier described with reference to FIG. 1.

Figure 12:
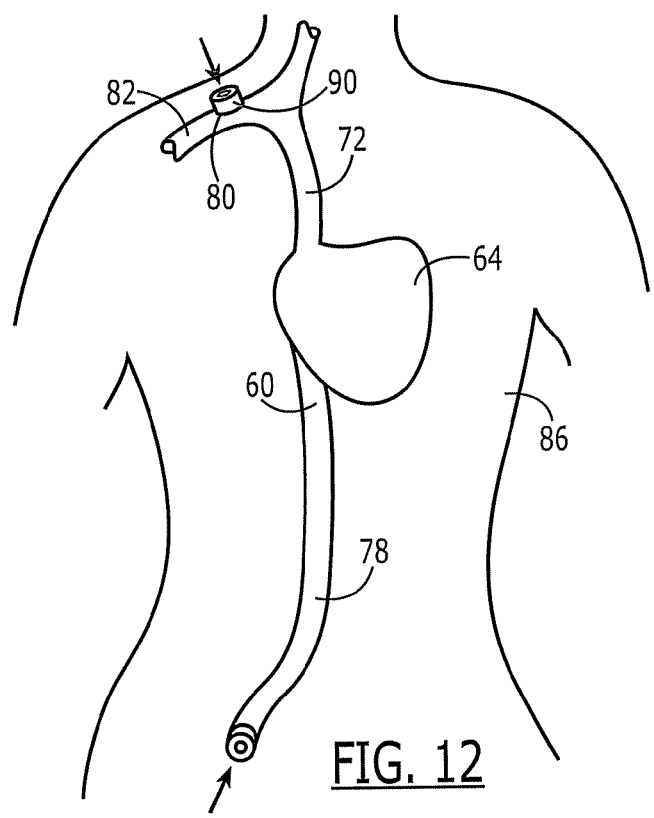
FIG. 12 is a diagrammatical illustration of a human body illustrating positions of catheter introducers in the subclavian vein and the femoral vein.
Figure 13:
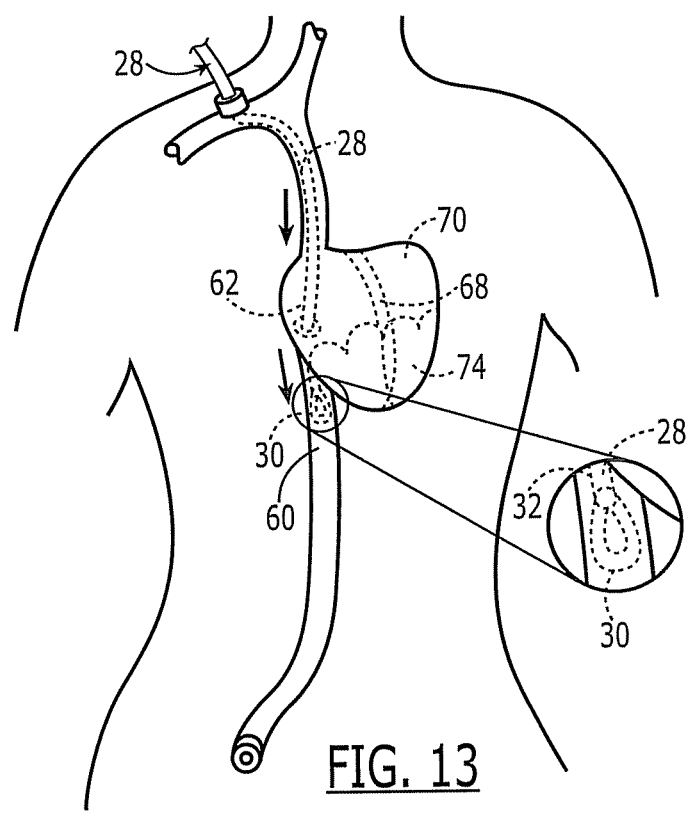
FIG. 13 is a diagrammatical illustration of the human body illustrating an insertion of a loop catheter into the subclavian vein, and identifying with dotted lines a section in the superior vena cava, the right atrium of the heart, and the insertion into the inferior vena cava, wherein an enlarged portion is illustrated in an exploded circular region.

With reference to FIG. 12, the puncture 80 is made to insert a catheter introducer 90 in a subclavian vein 82 of the body 86 of a patient. The loop catheter 28, earlier described with reference to FIG. 3, is passed through the catheter introducer 90 in the subclavian vein 82 and after passing along the superior vena cava 72, the loop catheter is inserted in the right atrium 62 of the heart 64 and passed into the inferior vena cava 60, where the loop 30 is moved downward into the inferior vena cava, as illustrated with reference to FIG. 13.

Figure 14:
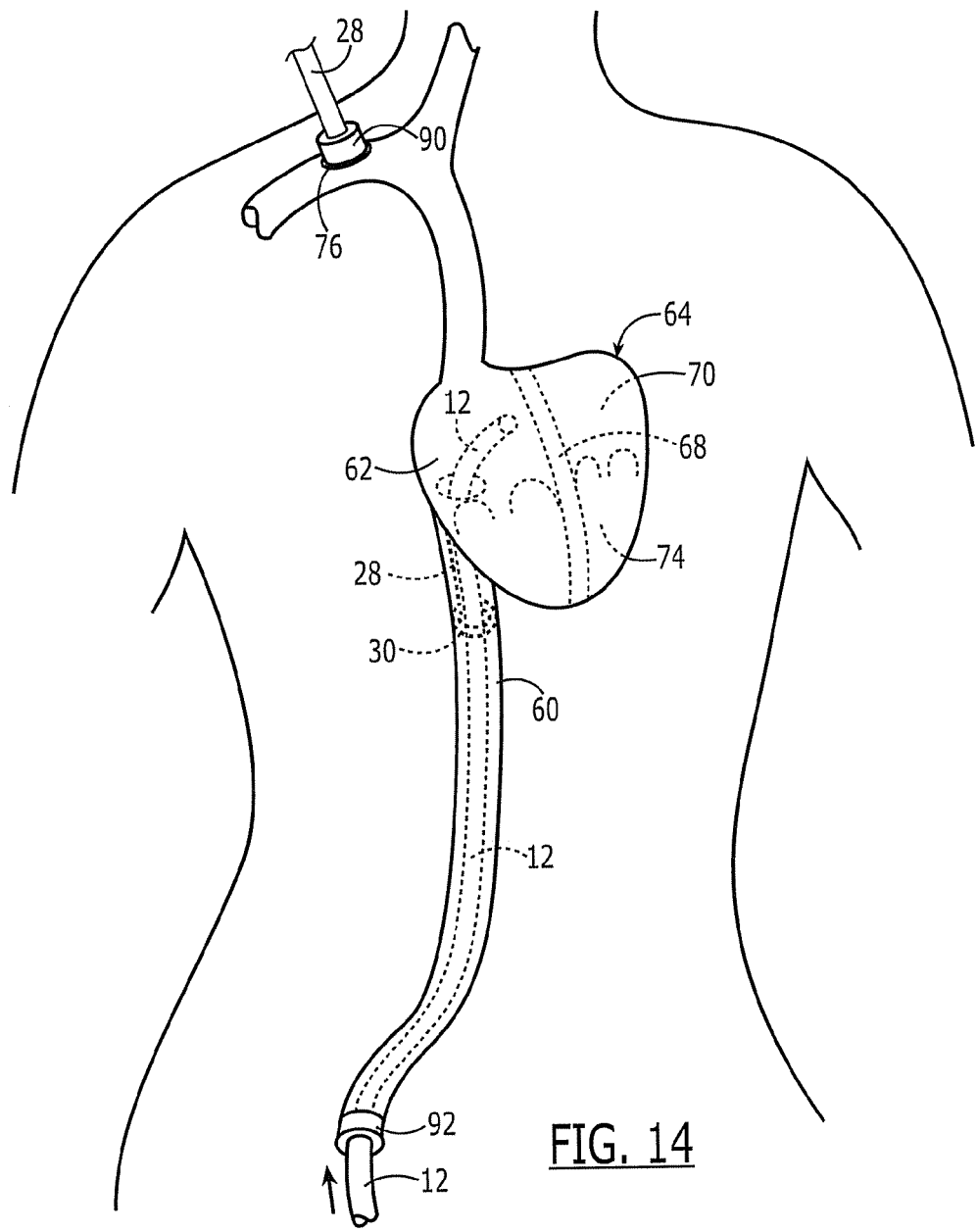
FIG. 14 is a diagrammatical illustration of the human body illustrating an introduction of the transseptal sheath by a femoral route until it reaches the right atrium of the heart as identified with dotted lines.
Figure 15:
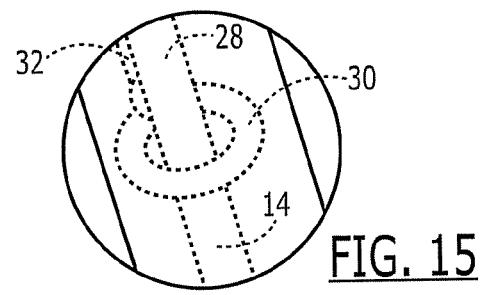
FIG. 15 illustrates an enlarged portion, as circled in FIG. 15, of the transseptal sheath loosely passing through the loop of the loop catheter while the loop is positioned in the inferior vena cava.

As illustrated with reference to FIG. 14, the transseptal sheath 12 is inserted by a femoral route by means of an appropriate catheter introducer 92, wherein the transseptal sheath is passed along the inferior vena cava 60 until the transseptal sheath reaches the right atrium 62 of the heart 64 after being passing through the loop 30 of the loop catheter 28, as illustrated with reference to FIG. 15, the loop catheter previously having been inserted into the inferior vena cava.

Forming the puncture 66 of the interatrial septum 68 may be performed with a Brockenbrough™ needle using traditional methods, wherein all conventional elements used to form the puncture are removed when the puncturing procedure is completed. It is well known in the art to use a transseptal introducer sheath and Brockenbrough™ needle to allow left atrial access from the venous system. Typically, the Brockenbrough™ curved needle is used in conjunction with transseptal catheters to puncture the atrial septum to allow conducting a left heart catheterization procedure through the right atrium.

Figure 16:
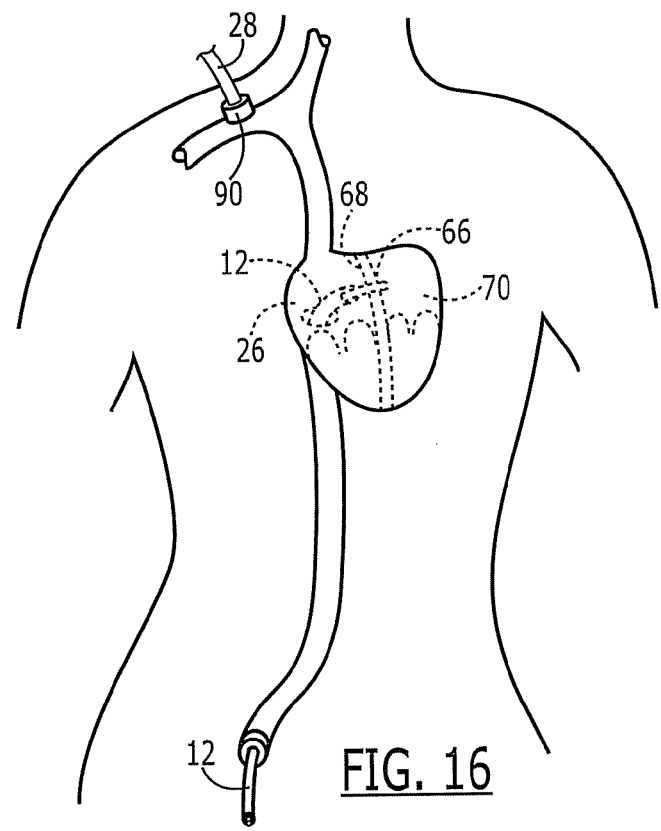
FIG. 16 is a diagrammatical illustration of the human body illustrating a puncture performed on the interatrial septum of the heart, which puncture may be made using a Brockenbrough needle, as identified with dotted lines.

As illustrated with reference to FIG. 16, once the puncture 66 of the interatrial septum 68 is made, the transseptal sheath 12 is passed through the puncture 66 from the right atrium 62 into the left atrium 70.

For the one embodiment herein described by way of example, the connector 36 is assembled with the cardiac catheter 14 by inserting it into the broadened portion 42 of the aperture 40 of the fastener 38 and the pulling element 20 is fixed to the fastener, as earlier described with reference to FIG. 1.

As earlier illustrated with reference to FIG. 1, the mandrel 44 is passed through the runner 22 and the fastener 38, and along the passage 34 of the cardiac catheter 14 until it reaches a distal end of the cardiac catheter. The mandrel 44 results in an integral connection between the runner 22, the fastener 38, the pulling element 20, and the cardiac catheter 14. These cooperating integrally connected elements are then inserted into the transseptal sheath 12, as illustrated with reference to FIG. 17.

Figure 17:
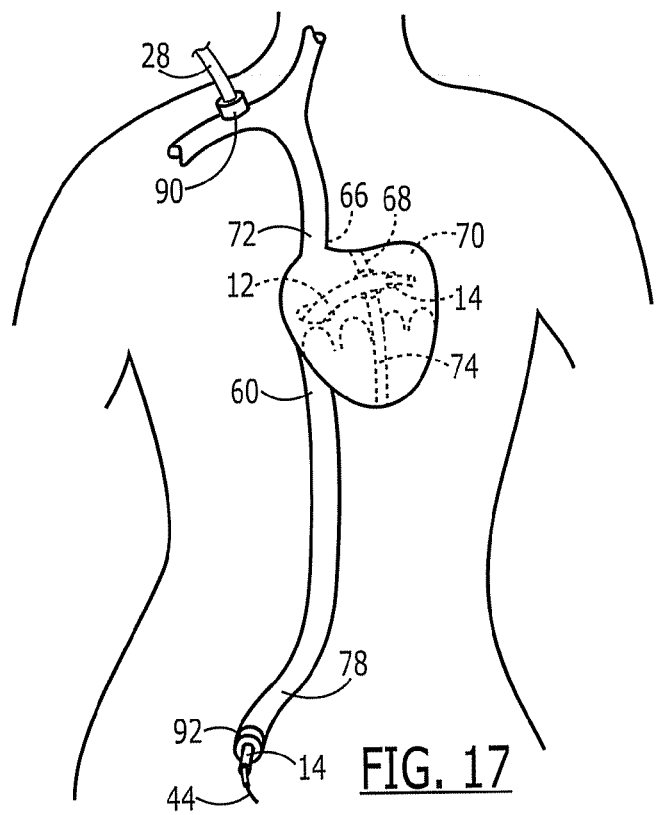
FIG. 17 is a diagrammatical illustration of a human body illustrating passage of the transseptal sheath into the left atrium, and the passage of the cardiac catheter, having the mandrel carried inside, by way of example for one embodiment, through the transseptal sheath, as identified with dotted lines.
Figure 18:
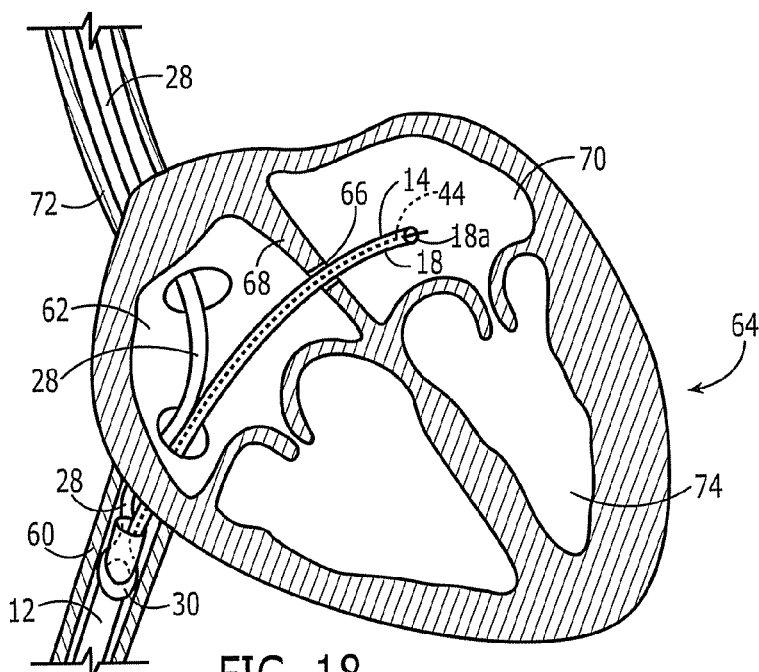
FIG. 18 is a diagrammatical cross sectional view of the heart illustrating the cardiac catheter having the mandrel therein, the cardiac catheter extending into the left atrium, and the transseptal sheath having been removed toward the inferior vena cava.

With continued reference to FIG. 17, by advancing the runner 22 forward toward the heart 64, the combination of elements including the fastener 38, the pulling element 20, the mandrel 44 and the cardiac catheter 14 is moved through the transseptal sheath 12 until the distal end 18 of the cardiac catheter 14 reaches the left atrium 70 of the heart. The transseptal sheath 12 is then removed from the heart 64 to the inferior vena cava 60 and held at a relatively short distance from the heart, as illustrated with reference to FIG. 18. During this partial removal of the transseptal sheath 12, by way of example for the embodiment herein described, the mandrel 44 has the role of keeping the cardiac catheter 14 steady and in place in the left atrium 70, or the left ventricle 74, as desired. As illustrated with continued reference to FIG. 18, the mandrel generally does not extend beyond the extreme edge 18A of the distal end 18 of the catheter 14.

Figure 19A:
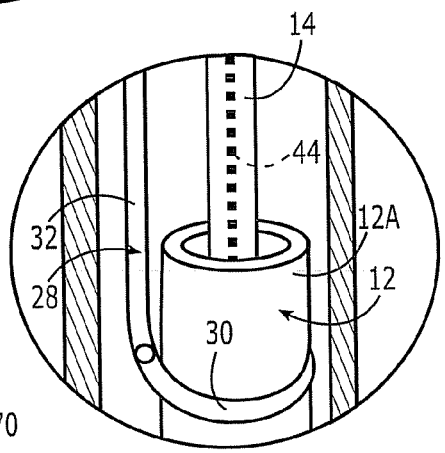
FIG. 19A illustrates a circled portion of the detail in FIG. 19, the mandrel identified with dotted lines and shown as being removed from the distal portion of the cardiac catheter toward to proximal portion, and near the loop of the loop catheter and the transseptal sheath loosely positioned within the loop.
Figure 19:
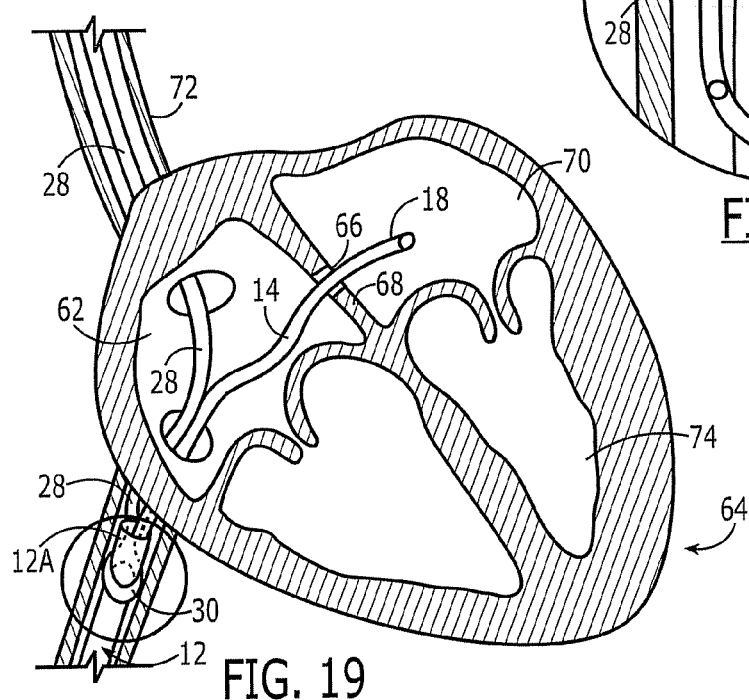
FIG. 19 illustrates the mandrel partially removed toward the proximal end of the cardiac catheter.

As illustrated with reference to FIG. 19, the mandrel 44 is then removed from the distal end 18 of the cardiac catheter 14 to the proximal end 16 of the cardiac catheter, wherein removing the mandrel 44 releases the cardiac catheter, which then becomes more flexible. As the mandrel 44 is partially removed from the cardiac catheter 14 outside the transseptal sheath 12, the cardiac catheter portion outside the sheath becomes flexible, while the proximal portion being carried inside the transseptal sheath remains relatively stiff. The runner 22 continues to be advanced along the transseptal sheath 12 and the fastener 38 is pushed until it reaches the inferior vena cava 60, and surpasses a distal end 12A of the transseptal sheath 12, leaving the pulling element 20 inside the loop 30 of the loop catheter.

Figure 20:
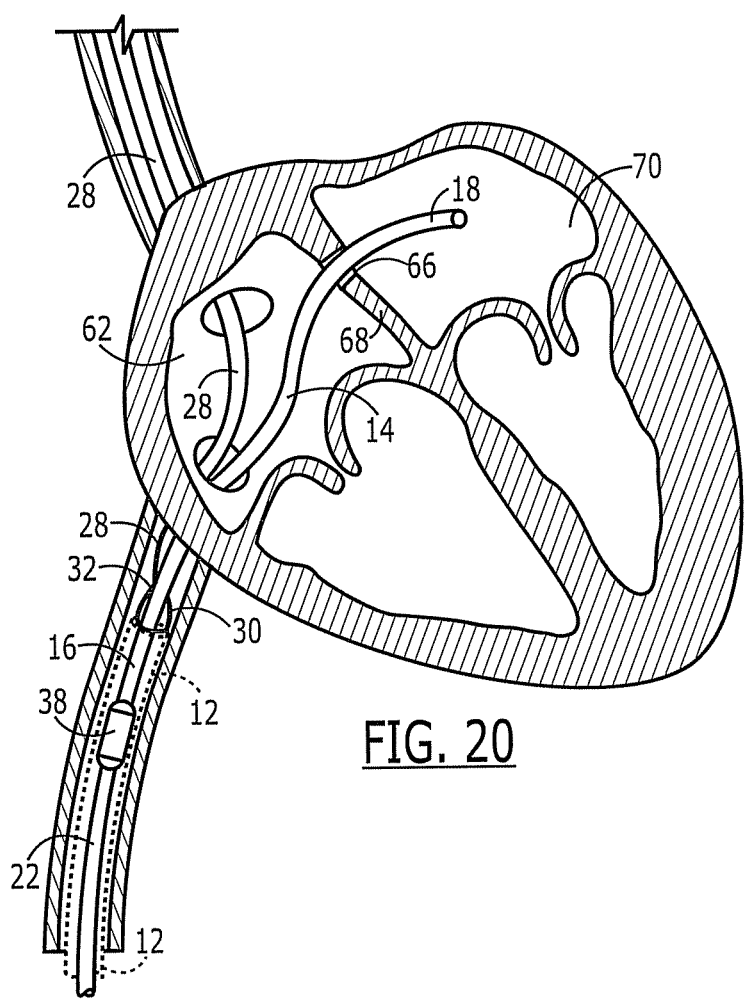
FIG. 20 is a partial cross sectional view illustrating the runner movable inside the transseptal sheath, and a pushing of the fastener and the pulling element toward the inferior vena cava.
Figure 21:
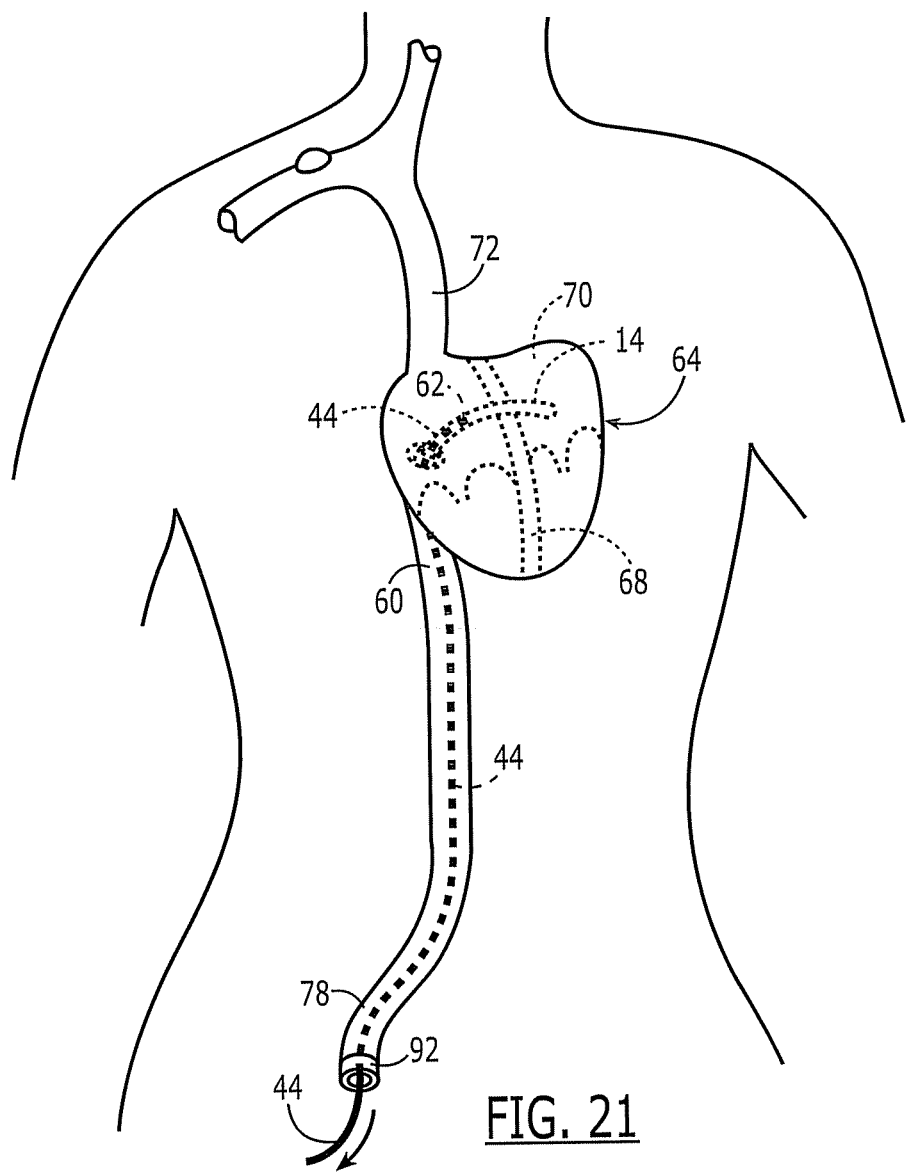
FIG. 21 is a diagrammatical illustration of the human body illustrating a complete retrograde removal of the mandrel by pulling the mandrel from the proximal end of the transseptal sheath.

The mandrel 44 is then completely removed from the cardiac catheter 14, the fastener 38 and the runner 22. This procedure detaches the runner 22 from the fastener 38, which runner remains inside the transseptal sheath 12, and leaves the proximal end 16 of the cardiac catheter 14 together with the pulling element 20 and the fastener 38 in the inferior vena cava 60, as illustrated with reference to FIGS. 20 and 21.

Figure 22:
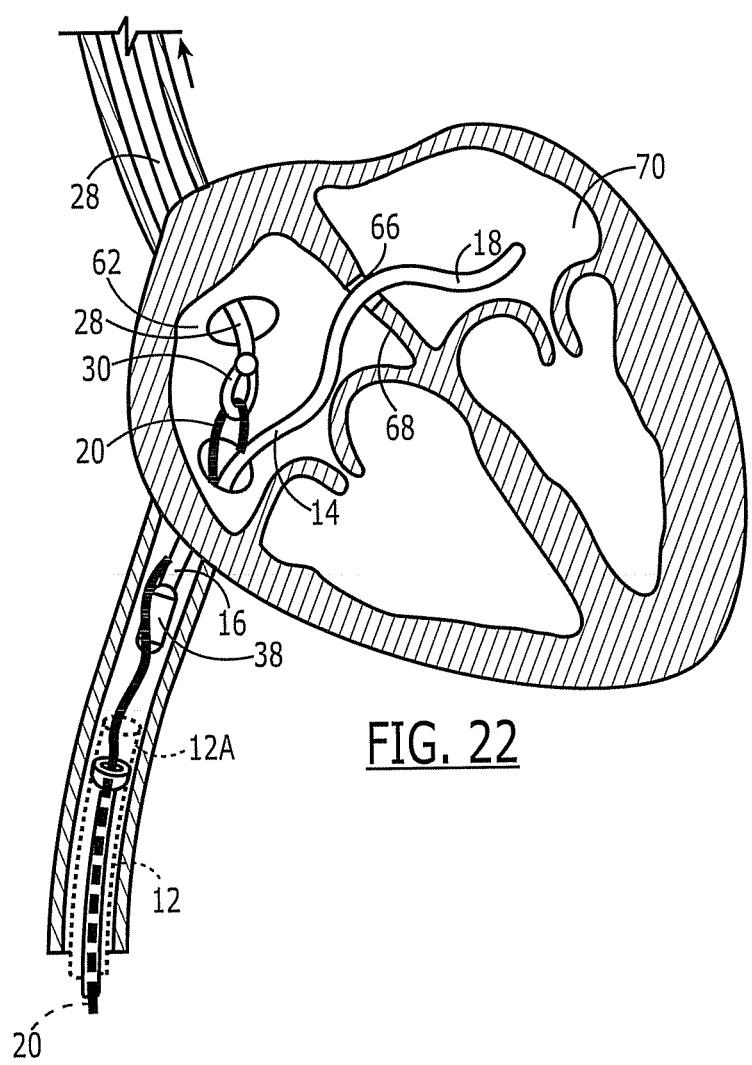
FIG. 22 is a cross-sectional view of the heart as in FIG. 19, now illustrating the loop catheter retrograde pull of the pulling element which pulling element is joined to the fastener and the proximal end of the cardiac catheter, the transseptal sheath remaining inside the inferior vena cava, the detached runner and the rest of the pulling element still remaining inside the transseptal sheath, wherein the removal of the mandrel illustrated in FIG. 21 disassembles the fastener from the runner, leaving the runner free inside the transseptal sheath and the fastener free inside the inferior vena cava.
Figure 23:
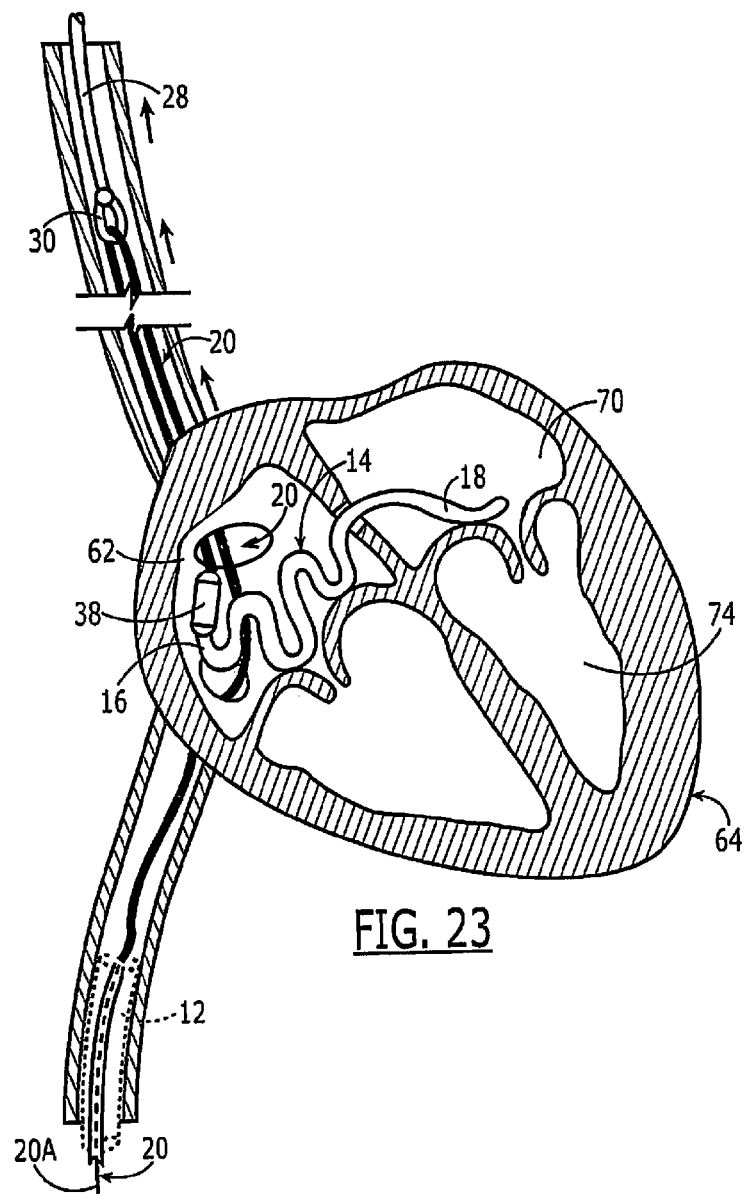
FIG. 23, to be considered sequentially after
Figure 24:
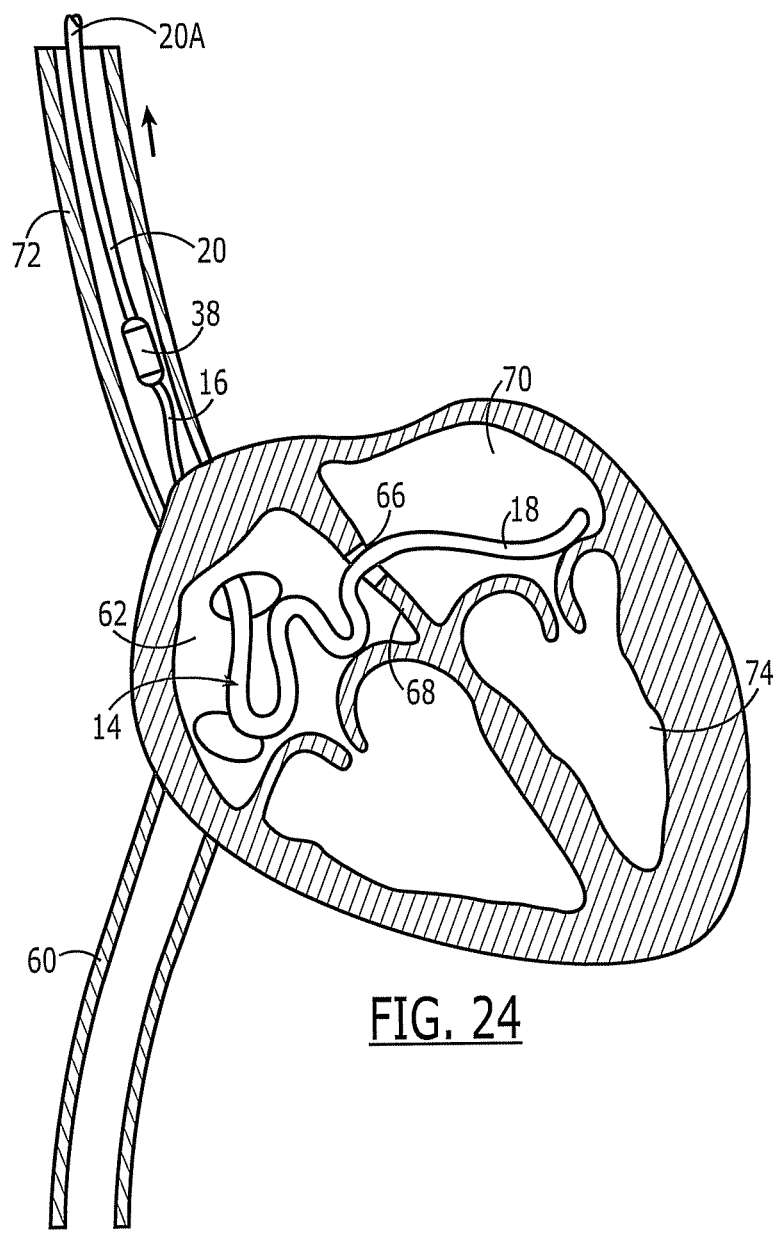
FIG. 24, to be further considered sequentially after

The loop catheter 28 is adjusted by holding the pulling element 20. Removal of the pulling element 20 is accomplished by pulling the loop catheter 28 into the right atrium 62 and further through the superior vena cava 72, as illustrated with reference to FIGS. 22, 23 and 24, until a free end 20A of the pulling element 20 is taken out through the catheter introducer 90 in the subclavian vein 82.

Figure 25:
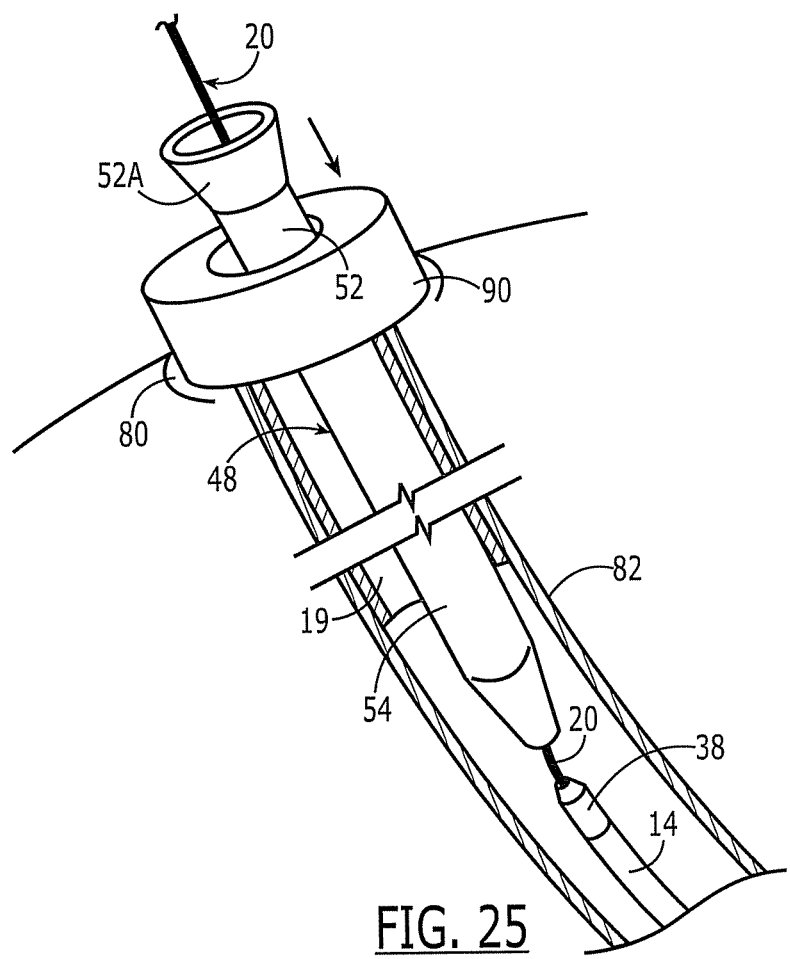
FIG. 25 is a cross-sectional view illustrating the subclavian vein and the superior vena cava with a catheter introducer inserted and an aligning element inserted into the catheter introducer, the pulling element is inserted into an internal passage of the aligning element, thus allowing a pulling thereof to pull the fastener and the proximal end of the cardiac catheter to a distal end of the aligning device to facilitate movement through the catheter introducer.

Eventually, and at an operator's discretion, the pulling element 20 can be taken out partially and cut, and then the cut section is taken out at the site of the femoral vein 78. The free end 20A of the pulling element 20 may optionally be inserted in the aperture 50 forming a passage through the aligning device 48 which is then inserted in the catheter introducer 90 of the subclavian vein 82 in order to align the fastener 38 connected to the proximal end 16 of the cardiac catheter 14 and allow its insertion into the catheter introducer 90 of the subclavian vein 82 for smooth removal, as illustrated with reference to FIG. 25.

Figure 26:
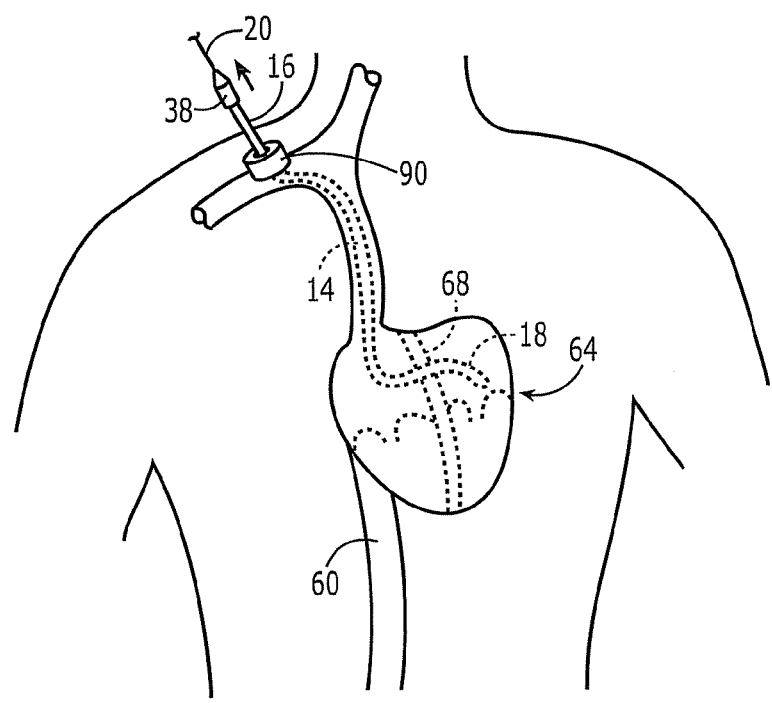
FIG. 26 is a diagrammatical illustration of the human body illustrating a retrograde removal of the fastener and the proximal end of the cardiac catheter through the catheter introducer, the desired localization of the opposing distal end of the cardiac catheter inside the superior vena cava and the left atrium or ventricle of the heart being identified with dotted lines.
Figure 27:
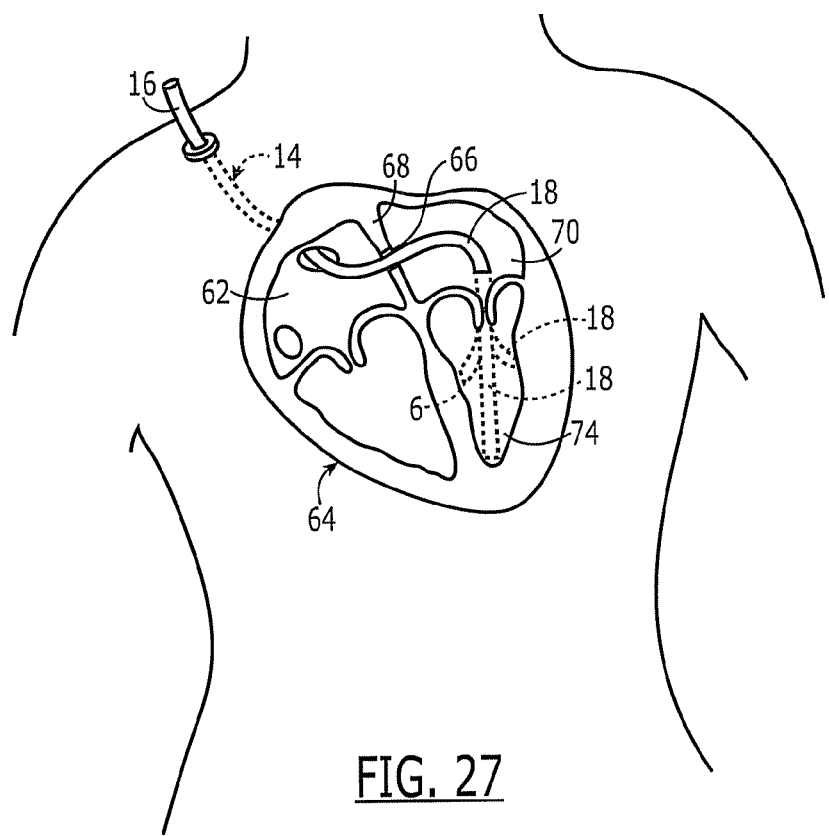
FIG. 27 is to be considered sequentially after

As illustrated with reference to FIGS. 26 and 27, the pulling element 20, the fastener 38 and the proximal end 16 of the cardiac catheter 14 are then completely removed through the catheter introducer 90 of the subclavian vein 82. The fastener 38 and the pulling element 20 are detached from the proximal end 16 of the cardiac catheter 14, and the connector 36 is left uncovered. Thus, the proximal end 16 of the cardiac catheter 14 may be brought outside the human body 86 through the subclavian vein 82, while the opposite end, the distal end 18 of the cardiac catheter 14, has been inserted in a chamber of the left atrium 70 or of the left ventricle 74 of the heart 64, as desired.

Figure 11:
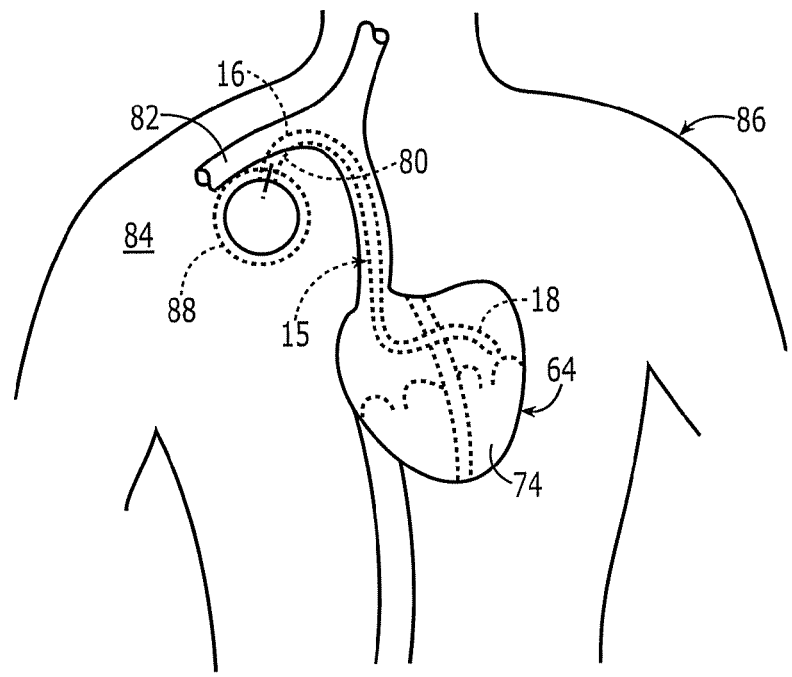
FIG. 11 a diagrammatical illustration of the human body illustrating results of a retrograde removal of the proximal end of the catheter and connection with a pacemaker or the like for operating with the distal end of the catheter located at a desired localization in the left atrium or left ventricle of the heart.

For the embodiment of the invention herein described, the procedure may be completed when the distal end 18 of the cardiac catheter 14 is placed in a desired position inside the left atrium 70 or the left ventricle 74 using customary techniques, and a pacemaker or any other implantable device 88, as earlier described with reference to FIG. 11, is implanted for operation with the proximal end 16 of the cardiac catheter 14 using customary procedures.

The constructive and functional advantages of this invention by which it is characterized are plain from the description above, representing a beneficial technological improvement that warrants the inclusion of the invention in the law with the pertinent legal protection as per the appended claims.

Indeed, many modifications and other embodiments of the invention will come to the mind of one skilled in the art having the benefit of the teachings presented in the foregoing description and the associated drawings. Therefore, it is to be understood that the invention is not to be limited to the specific embodiments disclosed, and that modifications and alternate embodiments are intended to be included within the scope of the claims supported by this specification.

That which is claimed is:

1. A device for positioning a cardiac catheter within a cardiovascular system, the cardiac catheter containing a connector at a proximal end thereof, and a first lumen extending longitudinally through the catheter and the connector, the device comprising:
    a fastener configured to be inserted into the cardiovascular system, the fastener having a second lumen extending longitudinally therethrough and an aperture extending partially therein receiving the connector therein and coupled thereto, wherein the first and second lumens are aligned; and
    an elongate, flexible pulling element coupled to the fastener and the connector for pulling thereof and thus pulling the cardiac catheter from the proximal end thereof.

2. The device according to claim 1, further comprising an elongate mandrel slidable within the lumens, wherein the mandrel keeps the cardiac catheter generally rigid along a central axis thereof to allow the cardiac catheter to move while avoiding kinking.

3. The device according to claim 2, wherein the mandrel comprises surgical wire.

4. The device according to claim 1, wherein the pulling element is coupled to the cardiac catheter through the connector and the fastener.

5. The device according to claim 1, wherein the elongate pulling element is coupled to the fastener at an end thereof.

6. The device according to claim 1, wherein the pulling element comprises at least one of surgical suturing, a wire, and a catheter.

7. A device comprising:
    a cardiac catheter including a connector at a proximal end thereof and a first lumen longitudinally extending through the connector and the cardiac catheter;
    a fastener configured to be inserted into a cardiovascular system, the fastener coupled to the connector, the fastener having a second lumen extending longitudinally therethrough, wherein the first and second lumens are aligned, the fastener including an aperture extending partially therein receiving the connector therein such that the connector is secured to the fastener within the aperture; and
    a flexible elongate pulling element coupled to the fastener and the connector.

8. The device according to claim 7, further comprising an elongate mandrel slidable within the lumens, wherein the mandrel keeps the cardiac catheter generally rigid along a central axis thereof to allow the cardiac catheter to move while avoiding kinking.

9. A device for positioning a cardiac catheter within a cardiovascular system, the device comprising:
    a connector dimensioned for connection to a proximal end of a catheter, wherein a first lumen longitudinally extends through the connector and the catheter;
    a fastener configured to be inserted into the cardiovascular system, the fastener coupled to the connector, wherein the fastener includes a second lumen aligned with the first lumen and an aperture extending partially therein structured for receiving the connector therein; and
    a flexible elongate pulling element coupled to the fastener and the connector for pulling thereof and thus the cardiac catheter from a proximal end thereof.

* * * * *